(12) United States Patent
Uri et al.

(10) Patent No.: US 8,196,416 B2
(45) Date of Patent: Jun. 12, 2012

(54) DEVICE FOR DIRECTIONAL COOLING OF BIOLOGICAL MATTER

(75) Inventors: Meir Uri, Kibbutz Bet Hashita (IL); Yaniv Damari, Ramat Gan (IL)

(73) Assignee: Core Dynamics Limited, Hamilton HM EX (BM)

( * ) Notice: Subject to any disclaimer, the term of this patent is extended or adjusted under 35 U.S.C. 154(b) by 433 days.

(21) Appl. No.: 10/588,077

(22) PCT Filed: Feb. 2, 2005

(86) PCT No.: PCT/IL2005/000123
§ 371 (c)(1), (2), (4) Date: May 1, 2007

(87) PCT Pub. No.: WO2005/072790
PCT Pub. Date: Aug. 11, 2005

(65) Prior Publication Data
US 2007/0277535 A1    Dec. 6, 2007

Related U.S. Application Data

(60) Provisional application No. 60/540,557, filed on Feb. 2, 2004.

(51) Int. Cl.
*F25D 13/06*    (2006.01)
(52) U.S. Cl. ......... 62/63; 62/64; 62/65; 62/374; 62/378; 62/130
(58) Field of Classification Search ............... 62/374, 62/378, 130, 63, 64, 65
See application file for complete search history.

(56) References Cited

U.S. PATENT DOCUMENTS

| | | | |
|---|---|---|---|
| 3,074,247 A * | 1/1963 | Polk | 62/63 |
| 3,347,745 A | 10/1967 | Rinfret et al. | |
| 4,018,911 A | 4/1977 | Lionetti et al. | |
| 4,117,881 A | 10/1978 | Williams et al. | |
| 4,480,682 A | 11/1984 | Kaneta et al. | |
| 4,620,908 A | 11/1986 | Van Duzer | |
| 4,857,319 A | 8/1989 | Crowe et al. | |
| 4,874,690 A | 10/1989 | Goodrich, Jr. et al. | |

(Continued)

FOREIGN PATENT DOCUMENTS

DE    10056181 C1 *    3/2002

(Continued)

OTHER PUBLICATIONS

Machine translation of Eck DE Publication No. 10056181C1.*

(Continued)

*Primary Examiner* — Cheryl J Tyler
*Assistant Examiner* — Jonathan Koagel
(74) *Attorney, Agent, or Firm* — Vorys, Sater, Seymour and Pease LLP; Susanne M. Hopkins; Ari G. Zytcer

(57) ABSTRACT

An apparatus for freezing a biological sample in a container while it moves along a cooling axis is provided. The apparatus has at least one set of two cooling plates with inner surfaces having a first plate dimension perpendicular to the axis, and a second plate dimension parallel to the axis. The inner surfaces define a passage therebetween with a width that corresponds to the container thickness and which is no larger than the first plate dimension. A method for cooling using the apparatus is also provided.

40 Claims, 5 Drawing Sheets

U.S. PATENT DOCUMENTS

| | | | |
|---|---|---|---|
| 5,059,518 | A | 10/1991 | Kortright et al. |
| 5,071,598 | A | 12/1991 | Baldeschwieler et al. |
| 5,131,850 | A | 7/1992 | Brockbank |
| 5,364,756 | A | 11/1994 | Livesey et al. |
| 5,418,130 | A | 5/1995 | Platz et al. |
| 5,587,490 | A | 12/1996 | Goodrich, Jr. et al. |
| 5,629,145 | A | 5/1997 | Meryman |
| 5,709,992 | A | 1/1998 | Rubinstein |
| 5,827,741 | A | 10/1998 | Beattie et al. |
| 5,843,780 | A | 12/1998 | Thomson |
| 5,863,715 | A | 1/1999 | Rajotte et al. |
| 5,869,092 | A | 2/1999 | Hays et al. |
| 5,873,254 | A * | 2/1999 | Arav ................................ 62/63 |
| 5,897,987 | A | 4/1999 | Oliver et al. |
| 5,955,257 | A | 9/1999 | Burger et al. |
| 6,007,978 | A | 12/1999 | Goodrich, Jr. et al. |
| 6,073,540 | A | 6/2000 | Garrett |
| 6,337,205 | B1 | 1/2002 | Wisniewski |
| 6,453,683 | B1 | 9/2002 | Wisniewski et al. |
| 6,482,585 | B2 | 11/2002 | Dottori |
| 6,723,497 | B2 | 4/2004 | Wolkers et al. |
| 6,740,484 | B1 | 5/2004 | Khirabadi et al. |
| 6,887,704 | B2 | 5/2005 | Peled et al. |
| 2002/0119946 | A1 | 8/2002 | Gen |
| 2002/0177116 | A1 | 11/2002 | Wiggins et al. |
| 2003/0059338 | A1 | 3/2003 | Mann et al. |
| 2003/0068416 | A1 | 4/2003 | Burgess et al. |
| 2004/0006999 | A1 | 1/2004 | Brown et al. |
| 2004/0067157 | A1 | 4/2004 | MacPhee et al. |
| 2004/0129003 | A1 | 7/2004 | Voute et al. |
| 2004/0191754 | A1 | 9/2004 | Meir et al. |
| 2004/0197310 | A1 | 10/2004 | Sanberg et al. |
| 2005/0008623 | A1 | 1/2005 | Bechetoille et al. |
| 2005/0020524 | A1 | 1/2005 | Boyd |
| 2005/0042754 | A1 | 2/2005 | Miyazaki et al. |
| 2005/0059152 | A1 | 3/2005 | Tanavde et al. |
| 2005/0095228 | A1 | 5/2005 | Fraser et al. |
| 2005/0142118 | A1 | 6/2005 | Wernet |
| 2006/0035383 | A1 | 2/2006 | Ho et al. |
| 2006/0057555 | A1 | 3/2006 | Damari et al. |
| 2007/0077237 | A1 | 4/2007 | Damari et al. |
| 2008/0120984 | A1 | 5/2008 | Shaham et al. |

FOREIGN PATENT DOCUMENTS

| | | |
|---|---|---|
| EP | 0 664 080 A1 | 7/1995 |
| EP | 0 668 013 A2 | 8/1995 |
| EP | 1 057 405 A1 | 12/2000 |
| EP | 1 131 998 A1 | 9/2001 |
| EP | 1 471 140 A1 | 10/2004 |
| EP | 1 535 514 A1 | 6/2005 |
| EP | 1 627 565 A1 | 2/2006 |
| GB | 1 279 356 | 6/1972 |
| JP | 2000-189155 A | 7/2000 |
| WO | 91/06213 A1 | 5/1991 |
| WO | 91/16060 A1 | 10/1991 |
| WO | 93/00806 A1 | 1/1993 |
| WO | 97/35472 A1 | 10/1997 |
| WO | 97/39104 A1 | 10/1997 |
| WO | 98/10231 A1 | 3/1998 |
| WO | 98/46072 A1 | 10/1998 |
| WO | 99/60849 A1 | 12/1999 |
| WO | 00/29551 A2 | 5/2000 |
| WO | 01/23532 A1 | 4/2001 |
| WO | 01/45503 A2 | 6/2001 |
| WO | 01/50852 A2 | 7/2001 |
| WO | 01/87062 A2 | 11/2001 |
| WO | 02/01952 A1 | 1/2002 |
| WO | 02/32225 A2 | 4/2002 |
| WO | 02/076206 A2 | 10/2002 |
| WO | 03/020874 A2 | 3/2003 |
| WO | 03/056919 A2 | 7/2003 |
| WO | 2004/009138 A2 | 1/2004 |
| WO | 2004/055456 A1 | 7/2004 |
| WO | 2004/098285 A2 | 11/2004 |
| WO | 2005/032251 A1 | 4/2005 |
| WO | 2005/056755 A2 | 6/2005 |
| WO | 2005/072523 A2 | 8/2005 |
| WO | 2005/072790 A1 | 8/2005 |
| WO | 2006/016372 A1 | 2/2006 |
| WO | 2008/032314 A2 | 3/2008 |

OTHER PUBLICATIONS

Ahlenstiel, et al., "Bioflavonoids attenuate renal proximal tubular cell injury during cold preservation in Euro-Collins and University of Wisconsin solutions", Kidney International, vol. 63, pp. 554-563, (2003). XP-002337114.

Chen, et al., "Beneficial Effect of Intracellular Trehalose on the Membrane Integrity of Dried Mammalian Cells", Cryobiology, vol. 43, pp. 168-181, (2001).

Chow, et al., "Phase I Pharmacokinetic Study of Tea Polyphenols following Single-dose Administration of Epigallocatechin Gallate and Polyphenon E", Cancer Epidemiology, Biomarkers & Prevention, vol. 10, pp. 53-58, (2001).

Crowe, et al., "Stabilization of membranes in human platelets freeze-dried with trehalose", Chemistry and Physics of Lipids, vol. 122, pp. 41-52, (2003).

Csönge, et al., "Banking of osteochondral allografts, Part II. Preservation of Chondrocyte Viability During Long-Term Storage", Cell and Tissue Banking, vol. 3, pp. 161-168, (2002). XP-002313332.

De Korte, et al., "Quality Determinants of Erythrocyte Destined for Transfusion", Cellular and Molecular Biology, vol. 50, No. 2, pp. 187-195, (2004).

Fujiki, et al., "Mechanistic Findings of Green Tea as Cancer Preventive for Humans", P.S.E.B.M., vol. 220, pp. 225-228, (1999).

Galati, et al., "Prooxidant activity and cellular effects of the phenoxyl radicals of dietary flavonoids and other polyphenolics", Toxicology, vol. 177, pp. 91-104, (2002).

Gao, et al., "Development of a Directional Solidification Device for Cell Cryopreservation", Cell Preservation Technology, vol. 1, No. 4, pp. 231-238, (2003).

Goodrich, et al., "Preservation of metabolic activity in lyophilized human erythrocytes", Proc. Natl. Acad. Sci. USA, vol. 89, pp. 967-971, (1992).

Grinberg, et al., "Protective Effects of Tea Polyphenols against Oxidative Damage to Red Blood Cells", Biochemical Pharmacology, vol. 54, pp. 973-978, (1997).

Han, et al., "Protection of osteoblastic cells from freeze/thaw cycle-induced oxidative stress by green tea polyphenol", Biotechnology Letters, vol. 27, pp. 655-660, (2005).

Higgs, et al., "Cartilage Regeneration and Repair, Where Are We?" Proceedings of the International Cartilage Repair Society's Second Symposium, (1998).

Isbrucker, et al., "Safety studies on epigallocatechin gallate (EGCG) preparations. Part 3: Teratogenicity and reproductive toxicity studies in rats", Food Chemical Toxicology, vol. 44, pp. 651-661, (2006).

Jomha, et al., "Cryopreservation of intact human articular cartilage", Journal of Orthopaedic Research, vol. 20, pp. 1253-1255, (2002).

Kumazawa, et al., "Direct Evidence of Interaction of a Green Tea Polyphenol, Epigallocatechin Gallate, with Lipid Bilayers by Solid-state Nuclear Magnetic Resonance", Biosci. Biotechnol. Biochem., vol. 68, No. 8, pp. 1743-1747, (2004).

Kusakabe, et al., "Maintenance of genetic integrity in frozen and freeze-dried mouse spermatozoa", Proc Natl Acad Sci U S A, vol. 98, No. 24, pp. 13501-13506, (2001).

Kushibe, et al., "Tracheal Allotransplantation Maintaining Cartilage Viability with Long-Term Cryopreserved Allografts", Ann Thorac Surg, vol. 71, pp. 1666-1669, (2001).

Laprade, et al., "Refrigerated Osteoarticular Allografts to Treat Articular Cartilage Defects of the Femoral Condyles. A Prospective Outcomes Study", J Bone Joint Surg Am, vol. 91, pp. 805-811, (2009).

Lelkens, et al., "Stability after thawing of RBCs frozen with the high- and low-glycerol method", Transfusion, vol. 43, pp. 157-164, (2003).

López, et al., "Determination of Viability of Human Cartilage Allografts by a Rapid and Quantitative Method Not Requiring Cartilage Digestion", Cell Transplantation, vol. 17, pp. 859-864, (2008).

McGoveran, et al., "Long-Term Chondrocyte Viability in a Fresh Osteochondral Allograft", The Journal of Knee Surgery, vol. 15, No. 2, pp. 97-100, (2002).

Muldrew, et al., "Localization of Freezing Injury in Articular Cartilage", Cryobiology, vol. 31, pp. 31-38, (1994).

Muldrew, "Cryopreservation of Articular Cartilage", Abstracts, 33rd Annual Meeting of the Society for Cryobiology, pp. 616-617, No. 6, Indianapolis, Indiana, Aug. 21, 1996.

Muldrew, et al., "Cryobiology of Articular Cartilage: Ice Morphology and Recovery of Chondrocytes", Cryobiology, vol. 40, pp. 102-109, (2000).

Muldrew, et al., "Transplantation of Articular Cartilage Following a Step-Cooling Cryopreservation Protocol", Cryobiology, vol. 43, pp. 260-267, (2001.

Muldrew, et al., "Chondrocyte Sensitivity to Lethal Injury Correlates with Proximity to the Cartilage Surface", Abstracts, 32nd Annual Meeting of the Orthopaedic Research Society, pp. 589, No. 136, New Orleans, Louisiana, Feb. 1986.

Pegg, et al., "Fractures in Cryopreserved Elastic Arteries", Cryobiology, vol. 34, pp. 183-192, (1997).

Rzepakovsky, "The Effect of Long Term Storage at −80° C. on the Cell Viabillity in Cartilage Tissue", Study Report, No. LAB-0161, 3 pages, (2005).

Rzepakovsky, "The Effect of Long Term Storage in Liquid Nitrogen on the Cell Viabillity in Cartilage Tissue", Study Report, No. LAB-0161, 3 pages, (2006).

Satpathy, et al., "Loading red blood cells with trehalose: a step towards biostabilization", Cryobiology, vol. 49, pp. 123-136, (2004).

Schachar, et al., "Transplantation of Cryopreserved Osteochondral Dowel Allografts for Repair of Focal Articular Defects in an Ovine Model", The Journal of Bone and Joint Surgery, Inc., vol. 17, pp. 909-920, (1999).

Dimethyl sulfoxide, SIGMA Product Information, 2 pages, Dec. 2003.

Suganuma, et al., "Green tea and cancer chemoprevention", Mutation Research, vol. 428, pp. 339-344, (1999).

Teng, et al., "Enhancing Osteochondral Allograft Viability", Clin Orthop Relat Res, vol. 466, pp. 1804-1809, (2008).

Towns, "Moisture content in proteins: its effects and measurement", Journal of Chromatography A, vol. 705, pp. 115-127, (1995).

Van Steensel, et al., "Optimization of cryopreservative procedures for human articular cartilage chondrocytes", Arch Orthop Trauma Surg, vol. 113, pp. 318-321, (1994).

Williams, et al., "Prolonged Storage Effects on the Articular Cartilage of Fresh Human Osteochondral Allografts", J Bone Joint Surg Am, vol. 85, pp. 2111-2120, (2003).

Williams, et al., "Analysis of Cartilage Tissue on a Cellular Level in Fresh Osteochondral Allograft Retrievals", Am J Sports Med, vol. 35, No. 12, pp. 2022-2032, (2007).

Williams, et al., "Controversies in Knee Surgery", Controversies in Orthopaedic Surgery, pp. 462-463, Oxford University Press, 2004.

XP-0023327043: Derwent, "Preservation solution for cells and tissues contains polyphenol as effective component", 1 page, (2002).

XP-002337044: Derwent, "Composition for preservative of animal cell, organs such as skin, blood vessel, cornea, kidney, heart, liver, lungs, placenta or pancreas, contains preset amount of epigallocatechin gallate as active ingredient", 1 page, (2003).

Zoberi, et al., "Radiosensitizing and anti-proliferative effects of resveratrol in two human cervical tumor cell lines", Cancer Letters, vol. 175, pp. 165-173, (2002).

* cited by examiner

DEVICE FOR DIRECTIONAL COOLING OF BIOLOGICAL MATTER

CROSS REFERENCE

This is a National Phase Application filed under 35 U.S.C. 371 of International Application No. PCT/IL2005/000123, filed Feb. 2, 2005, claiming the benefit under 35 USC 119(e) of U.S. Provisional Application No. 60/540,557, filed Feb. 2, 2004, the entire contents of each of which is hereby incorporated herein by reference in its entirety.

FIELD OF THE INVENTION

This invention relates to controlled freezing biological material, and more particularly to a directional freezing device adapted for that purpose.

BACKGROUND OF THE INVENTION

Transfusion of blood to someone who has suffered an injury or undergone a medical procedure resulting in blood loss is a well known and common practice. The transfused blood is typically donated by volunteers, and collected by organizations such as the International Red Cross, Magen David Adom, and private collection centers. Levels of blood donation are seasonal, dropping at certain times during the year, and are also affected by major events, such as the Sep. 11, 2001 attacks on the United States. After such well-publicized events, blood donations tend to soar, often irrespective of need (after the Sep. 11, 2001 attacks on the United States, for example, over half a million units were donated, while fewer than 300 were used for those injured in the attacks). Methods have been developed to store donated blood for future need.

Fresh Red Blood Cells (RBC) can be refrigerated for up to 42 days, after which they are discarded due to RBC recovery falling below 70% (for this reason, over 200,000 units of blood were discarded following the September 11 attacks). Frozen RBC units can be stored for up to 10 years.

During freezing of blood, the rate of cooling affects the morphology of the intracellular ice crystals. Maximizing the survival rate of RBCs requires careful control of the freezing process. Conventional freezing devices involve lowering the temperature of the chamber in a controlled stepped manner. The thermal gradient within the sample is determined implicitly by the temperature of the chamber and the thermal conductivity of the materials of the sample, and is not directly controllable.

U.S. Pat. No. 5,873,254 discloses a device for controlled freezing and warming of a biological sample, and freezing and thawing protocols for which the device is well suited. The device establishes a laterally varying thermal gradient and provides a mechanism for moving the sample along the thermal gradient at a controlled rate of speed. The sample is moved along the thermal gradient at a rate of speed that provides a variable cooling rate or a variable warming rate in accordance with the appropriate protocol. The device also allows continuous seeding of the sample through the freezing process at the exact freezing point of the solution. Real time monitoring and video imaging of the freezing process enable fine tuning of the thermodynamic parameters for improved control. However, the device is suited for small samples.

WO 03/056919 disclose a method for changing the temperature of a sample from an initial temperature via an intermediate temperature to a final temperature. Either the initial or the final temperatures is above the freezing point of said sample and the other is below the freezing point. The method is for changing the temperature of a sample having minimal dimension in each of two mutually perpendicular cross-sections exceeding 0.5 centimeters, and at least one of the cross-sections has an outer zone and an inner zone.

SUMMARY OF THE INVENTION

According to one aspect of the present invention, there is provided an apparatus for freezing a biological sample in a container while it moves along a longitudinal axis of the apparatus. The container has a first container dimension perpendicular to the axis, a second container dimension parallel to the axis, and a container thickness. The first container dimension is defined by the maximum level which the sample may have along the dimension. The apparatus comprises at least one set of two cooling plates with inner surfaces having a first plate dimension perpendicular to the axis, and a second plate dimension parallel to the axis. The inner surfaces define a passage therebetween whose width corresponds to the container thickness and which is no larger than the first plate dimension. The first plate dimension is at least as large as the level of the biological sample along the first container dimension during use. The apparatus further comprises a motion unit adapted for movement of the container through the passage along the axis so as to allow cooling of the sample by conduction from the inner surfaces of the plates.

An apparatus according to the present invention has several advantages. One of the advantages is that it allows for the possibility of large-scale freezing of biological samples using a directional freezing technique.

The apparatus is designed so that the inner surfaces of the plates are parallel to side walls of the containers, and preferably so as to facilitate the movement of the container through the passage. This includes, but is not limited to, ensuring a constant cross section throughout the length of the passage, and providing smooth inner surfaces.

In order to facilitate cooling of the biological sample, each cooling plate may comprise at least one channel adapted for flow of a cryogenic fluid, such as liquid nitrogen, essentially along both plate dimensions. However, the cooling may be accomplished by any suitable means, including, but not limited to, externally mounted tubes adapted for flow of cryogenic fluid therethrough. In addition, there may be provided a heating arrangement, such as electric resistance heaters, in order to better control the cooling process. The apparatus may further have associated with it a feedback control system and monitoring means.

According to one embodiment of the present invention, the cooling plates are arranged in a vertical configuration in which the plates are parallel to each other, and their heights, constituting the first plate dimension, define the maximum first container dimension. According to another embodiment, the cooling plates are arranged in a horizontal configuration, in which one plate is disposed parallel above the other, and their widths, constituting the first plate dimension, define the maximum first container dimension.

According to another aspect of the present invention, there is provided a method of cooling a biological sample. The method comprises providing an apparatus as described above, inserting therein a container containing a biological sample to be frozen, providing a predetermined temperature gradient along the axis, and moving the container through the passage along the axis.

BRIEF DESCRIPTION OF THE DRAWINGS

In order to understand the invention and to see how it may be carried out in practice, embodiments will now be described, by way of non-limiting examples only, with reference to the accompanying drawings, in which.

DETAILED DESCRIPTION OF THE INVENTION

Figure 1:
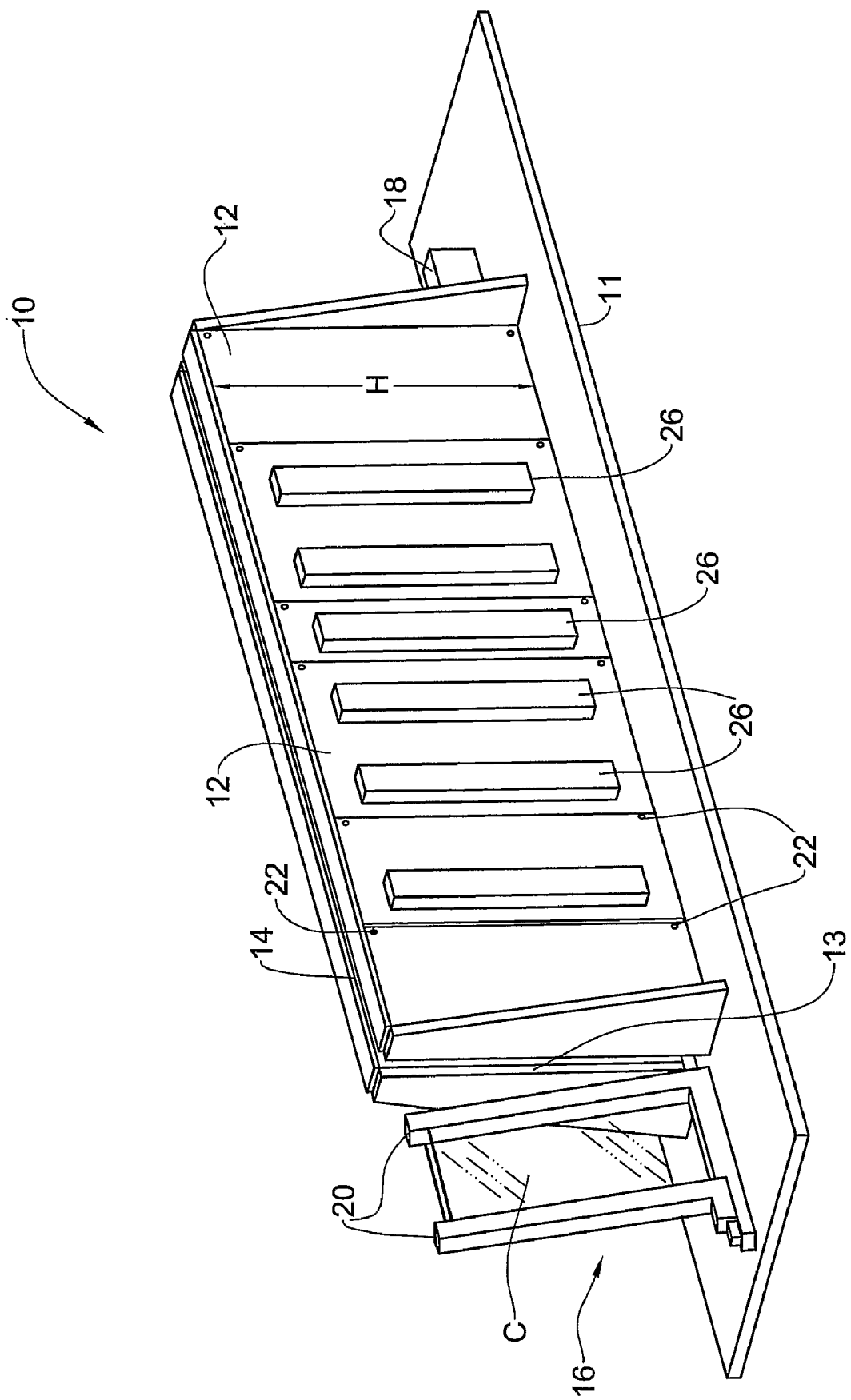
FIG. 1 is a perspective view of an apparatus according to one embodiment of the present invention.

FIG. 1 illustrates a freezing apparatus 10, adapted to freeze a container C containing a biological sample (not shown), according to one embodiment of the present invention. The freezing apparatus 10 comprises a base 11 and a plurality of vertically oriented plates 12 mounted thereon parallel to longitudinal axis X of the device on both sides thereof. Inner surfaces 13 of the plates define between them a narrow passage 14 of width W which is throughout their length along the axis X. It should be noted that the width W may be adjustable. The plates' height H is greater than the width W of the passage, and may be as small as twice the size thereof.

There is further provided a retention device 16 adapted to grasp the container C and a motion unit 18 for moving the retention device through the passage 14. The motion unit 18 is adapted to move the retention device 16 at various speeds along the passage 14. According to this embodiment, the retention mechanism comprises two vertical prongs 20, spaced by a distance L, at least one of which may be movable to adjust the distance L to suit the container's dimension along the axis X. As shown, the container is received between the prongs 20 so as to thermally contact the inner surfaces 13 when inserted, to be cooled by conduction. It should be noted that hereinafter in the specification and claims, the term contact should be understood to mean any contact, direct contact or abutting contact, with or without intermediate agent or means.

In order to facilitate easy movement of the container C through the passage, while not adversely affecting the cooling, at least one of several features may be present. The container C and the inner surfaces 13 may be smooth, further allowing tight contact between the inner surfaces 13 and the container C when the container passes through the passage. The container C is preferably flexible, so as to allow even distribution of the sample against both inner surfaces 13.

Alternatively, there may be two thin sheets of a thermoconductive material (not shown) extending between the prongs, or one sheet wrapped around them, defining a rectangular box-shaped void for retaining therein the container. The width of the prongs 20 of the retention device 16 is such so that it slidingly fits within the passage 14. It should be noted that the thin sheets, if provided, serve the dual purpose of retaining the container within the retention device 16 before it is moved within the passage 14 and preventing the container from sticking to the plates 12 during freezing. The first need may be obviated by initially moving the retention device 16, without the container C, into the passage 14 and then placing the container therein through the open top of the passage, or by making the container of a stiff-walled container which is adapted to maintain its shape in the absence of such thin sheets. The second need may be obviated by using a container which is adapted not to stick to the plates 12 during freezing, or by use of the freezing apparatus under conditions, such as low humidity, such that the sticking does not occur.

Figure 2A:
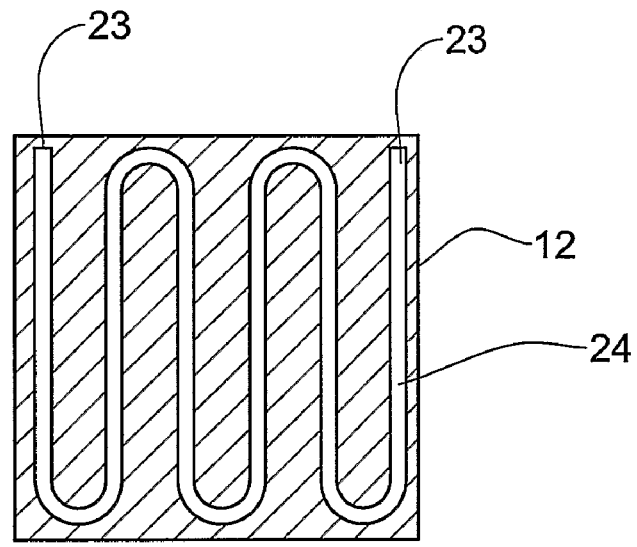
FIGS. 2A and 2B are cross-sectional views of plates according to the present invention.
Figure 2B:
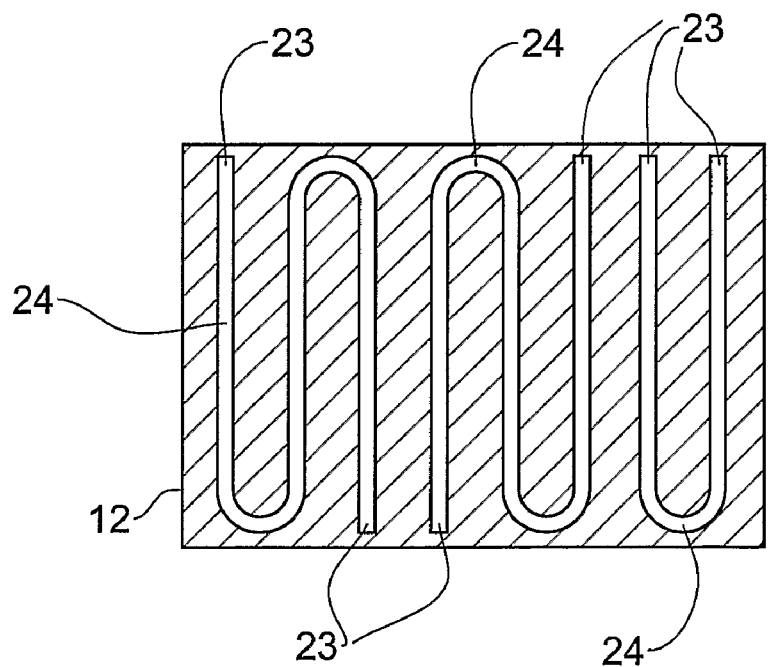

The plates 12 are of a thermoconducting material, preferably brass, although other suitable materials, such as, but not limited to, aluminum, may be used. The plates 12 comprise channels 24 (seen in FIGS. 2A and 2B) formed therein. Upstream and downstream endpoints 23 of the channels are in sealed fluid communication with connections 22, adapted for ingress and egress of a cryogenic fluid such as liquid nitrogen (LN). A first connection of the pair serves as an inlet for the cryogenic fluid and a second connection serves as an outlet. It should be noted that each plate 12 may comprise one or more channels 24. The plates 12 further comprise heating elements 26, which are typically electrical resistance heaters, adapted to further control the temperature, as described in more detail below.

Since the plates 12 are adapted to cool by conduction, it is important to maintain direct contact between them and the container C. There may therefore be provided a mechanism for ensuring that the plates maintain a tight contact even during expanding and contracting of the biological sample within a flexible container. The plates 12, at least on one side, may be mounted on springs in order to automatically adjust to the varying width of the container C and maintain direct contact. Alternatively, the plates 12 themselves may be constructed so that the inner surfaces 13 thereof are biased on springs toward the direction of the passage 14.

Figure 3:
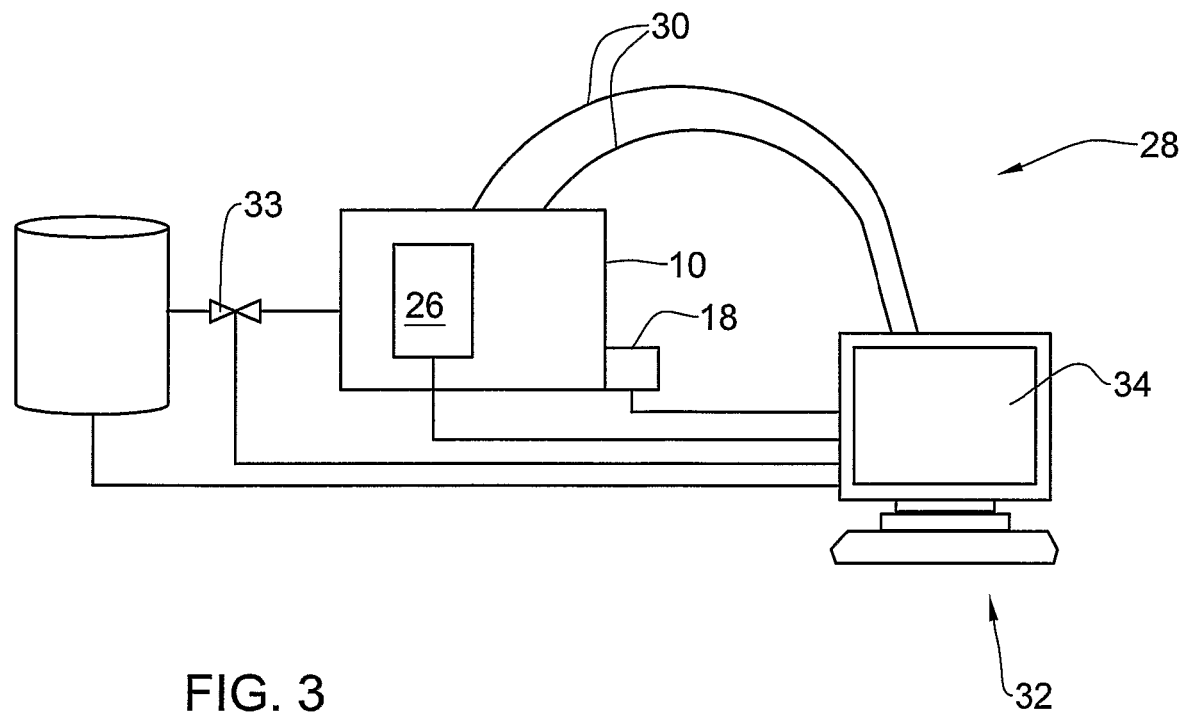
FIG. 3 is a schematic view of a feedback loop according to the present invention.

As illustrated in FIG. 3, the freezing apparatus 10 further comprises a feedback loop 28. Typically, the feedback loop ensures that an appropriate temperature gradient is provided by the freezing apparatus. The feedback loop 28 comprises temperature sensors 30, which are preferably thermocouples, disposed in strategic locations along the inner surfaces 13 of the plates 12. The temperature sensors 30 are attached, either directly or indirectly, to a processing unit 32. The processing unit 32 is preferably a PLC, but may be any suitable device, such as a computer having control software. The processing unit 32 is preferably capable of controlling the flow of the cryogenic fluid by independently controlling several cryogenic valves 33 in order to produce a preferred temperature gradient along the length of the passage 114. It should be noted that this may be a non-uniform gradient, i.e., where the temperature change per linear distance changes over the length of the axis, or a zero gradient, i.e., where the temperature is constant along the entire length of the axis. The processing unit 32 is also preferably adapted to control the pressure in the supply tank of cryogenic fluid, the heating elements 26, and may be adapted to control the operation of motion unit 18. It may further be adapted to be preloaded with information concerning the size of the sample, desired end temperature, and one or more specific freezing protocols, which may vary depending on the type of biological sample being frozen and/or its intended use. The processing unit 32 may be provided with a display 34 adapted for displaying relevant parameters thereon. The display 34 may be a touch-sensitive screen. The processing unit 32 is also preferably adapted for documenting the freezing process.

Figure 4A:
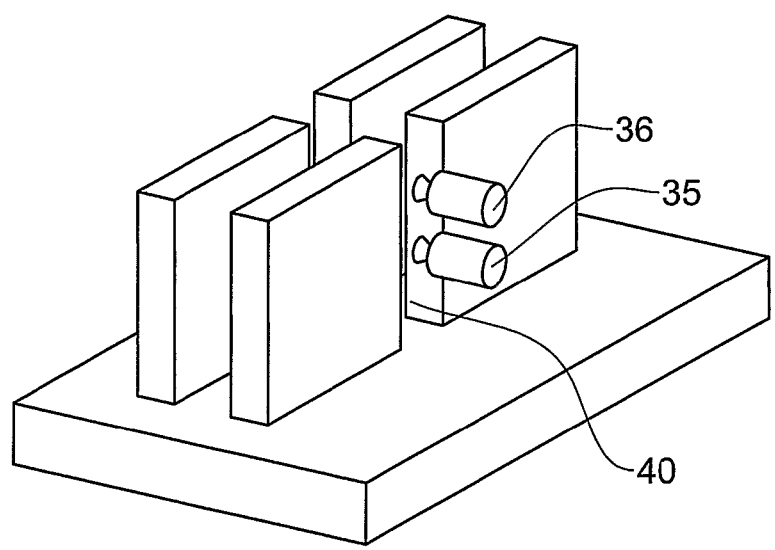
FIG. 4A is a schematic view of monitoring means according to the present invention.
Figure 4B:
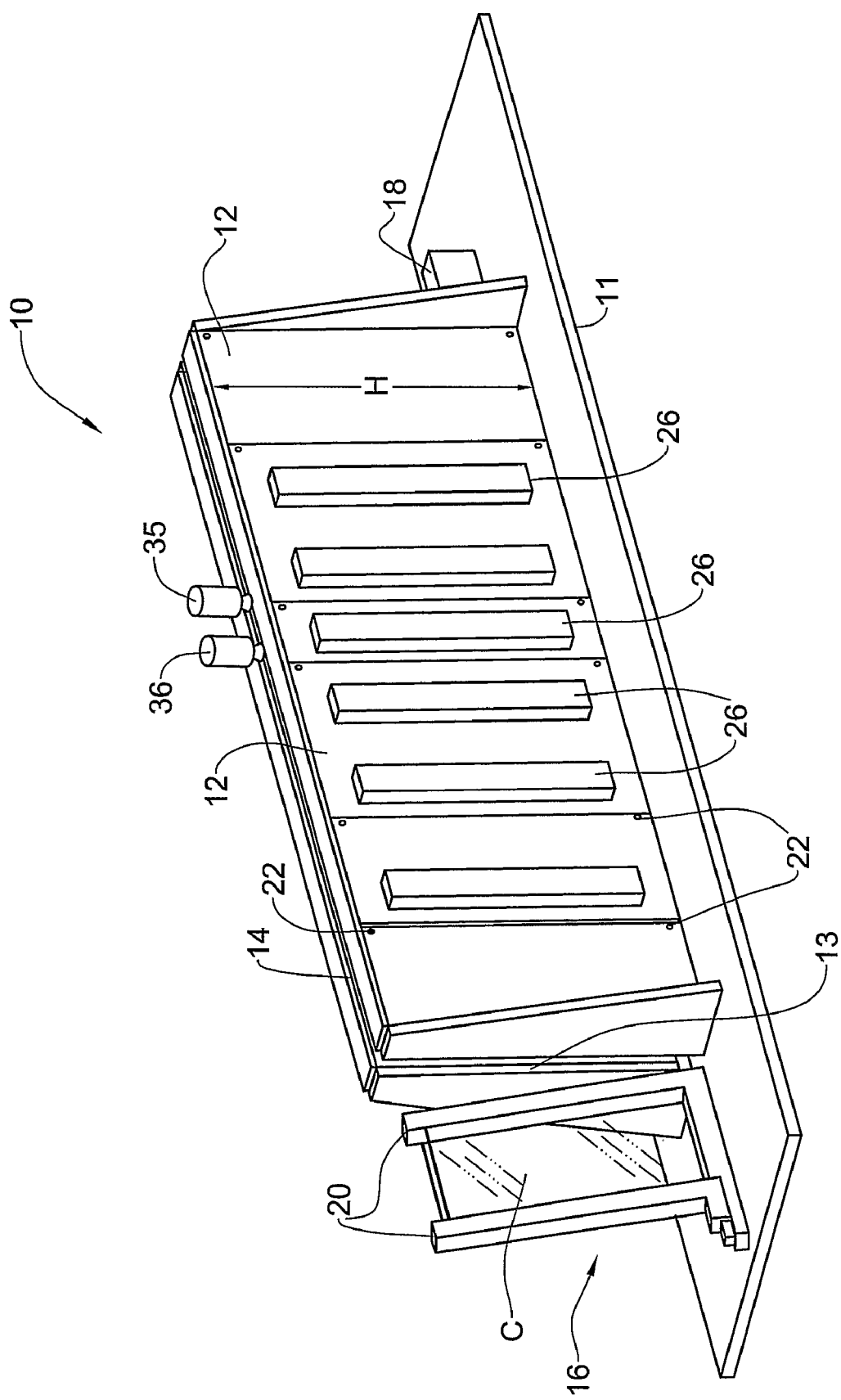
FIG. 4B is a schematic view of an alternative arrangement of monitoring means according to the present invention.

As seen in FIG. 4A, the plates may be arranged with gaps 40. In such a case, the freezing apparatus 10 may further comprise monitoring means, which may be disposed in the gaps 40. However, it should be noted that the monitoring means may be arranged above the passage 14, as seen in FIG. 4B, without including gaps. However, the first arrangement has the advantage that the center of the sample is more easily monitored, which, due to the absence of boundary effects inherent with viewing the top edge of the container, is more representative of the condition of the majority of the sample during freezing. The image from the video camera and/or the readings from the thermographs may be presented on the display 34 of the processing unit or on an independent monitor (not shown).

Freezing a biological sample using a freezing apparatus as described above has the advantage that a relatively narrow yet optionally tall container can be used, and still achieve controlled freezing of a large biological sample in a directional manner without extensive damage to cells. For example, a container with dimensions of 10 mm width ×200 mm height ×300 mm depth can be used to freeze a 600 ml sample using the freezing apparatus as seen in FIG. 1.

Figure 5:
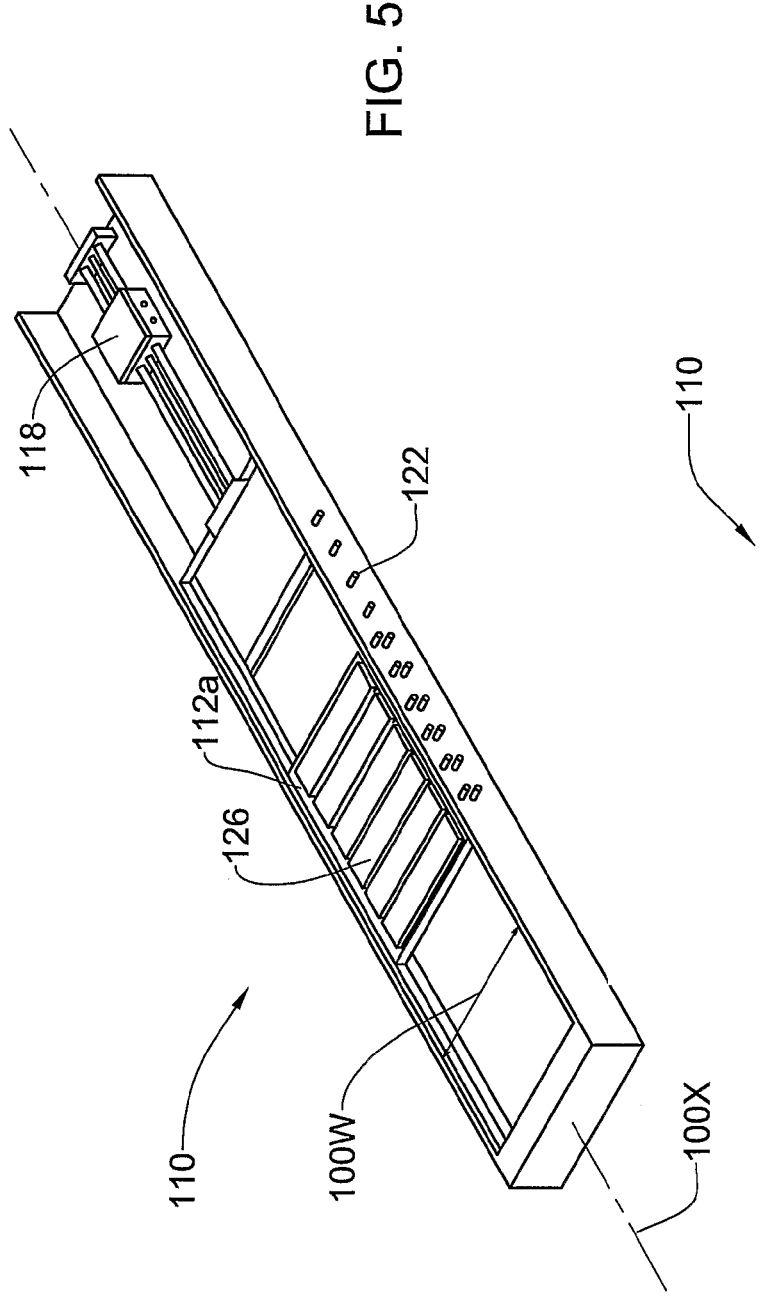
FIG. 5 is a perspective view of an apparatus according to another embodiment of the present invention.
Figure 6:
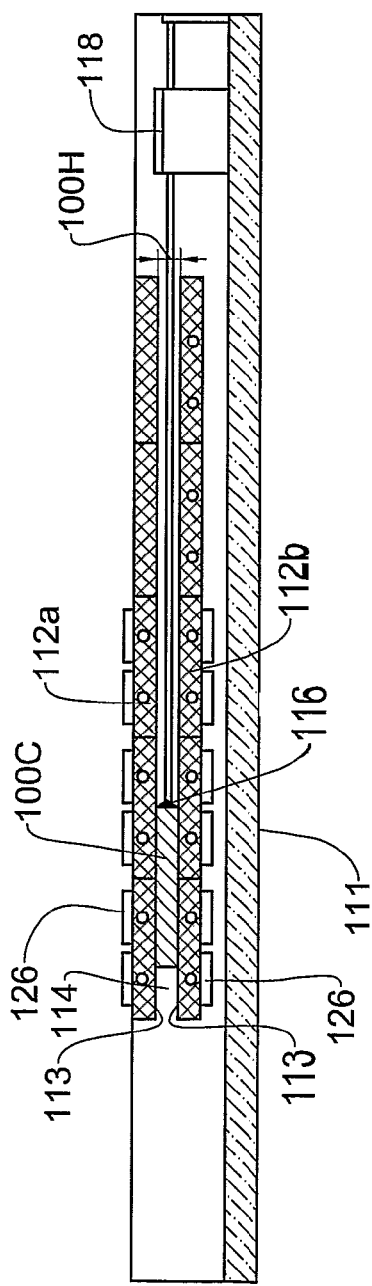
FIG. 6 is a close-up and partially sectioned view of the apparatus of FIG. 5.

FIGS. 5 and 6 show another embodiment of a freezing apparatus of the present invention. For the sake of clarity, elements in the freezer which are similar to elements disclosed in connection with the previous embodiment of FIG. 1 are designated with the same reference numbers shifted by 100.

A freezing apparatus 110 is adapted to freeze a container 100C containing a biological sample. The freezing apparatus 110 according to the present embodiment comprises a base 111 and a plurality of horizontally arranged plates 112 mounted thereon parallel to an axis 100C on both sides thereof. Upper plates 112a are disposed opposite corresponding lower plates 112b. Inner surfaces 113 of the plates define between them a narrow passage 114 of essentially constant height 100H, at least during use, throughout their length along the axis 100X. The upper plates 112a are supported from above by springs (not shown). The springs ensure that a full contact is maintained between the upper plate 112a and the container. The plates' width 100W is greater than the height 100H of the passage, and may be as small as twice the size thereof. The container 100C and the narrow passage 114 are smooth so that there is tight contact between the inner surfaces 113 and the container 100C when the container passes through the passage.

There is further provided a clasp 116 adapted to grasp the container 100C and a motion unit 118 for moving the retention device through the passage 114. According to this embodiment, the clasp is adapted to pull the container along the axis 100X.

Although not specifically shown in the figures with reference to the present embodiment, it should be noted that heating and cooling means, as well as feedback and monitoring means, may be provided similarly as in the first embodiment as shown in FIGS. 1 through 4.

According to any one of the above embodiments, the narrow passage may be divided into three functional areas. The first area is designated as the initial chamber. In this area, the container is initially received, and the sidewalls of the passage 14 may be made of thermally insulating material. The initial chamber may be adapted to hold the container at a predetermined temperature. In addition, the freezing process may be initiated here by seeding. Seeding is accomplished by freezing a very small area of the container C, for example, with the cryogenic fluid. It should be noted that the freezing apparatus may be adapted to perform the seeding internal to the chamber, such as described, or external to the chamber, using any device suited for that purpose.

When the seeding is done externally, the container should be positioned is such a way so that the freezing is initiated at a top part of the container. This ensures that the area where seeding is accomplished is largely free of living cells. Before or upon introduction into the passage, the container is rotates so that the area where the seeding had been accomplished is at the front in the direction of motion.

The second functional area is designated as the freezing block. In this area, the plates 12 are designed to freeze the biological sample as described above.

The third functional area is referred to as the collection chamber. This area is adapted for removal of the container from the device. In addition, the biological sample may be further cooled to extremely low temperatures suitable for long-term storage. In this area, one or more of the plates 12 may be made from a thermally insulating material.

The freezing apparatus according to any of the above embodiments may be used or constructed in such a manner such that the longitudinal axis is oriented vertically. In such a setup, the gradient should be such that the temperature is lower the higher along the axis the container travels. The container therefore is moved upwardly along the axis. This is particularly important when seeding is done internally, since this orientation allows for the cells to descend in the container, and the freezing process is initiated in an area which is largely liquid and devoid of living cells. It should be noted that when the seeding is accomplished externally as described above, the gradient may be oriented so that the container is moved upwardly or downwardly along the axis.

Those skilled in the art to which this invention pertains will readily appreciate that numerous changes, variations and modifications can be made without departing from the scope of the invention mutatis mutandis. For example, the freezing apparatus is not limited to having a plurality of plates. It may be constructed using only two plates, one on each side of the narrow passage.

The invention claimed is:

1. An apparatus for freezing a biological sample in a flexible container, the apparatus comprising:
   a cooling axis;
   at least one set of two cooling plates with inner surfaces positioned along the cooling axis, each at least one set of two cooling plates comprising
      a first plate dimension perpendicular to the cooling axis, and a second plate dimension parallel to the cooling axis;
      a passage defined between the inner surfaces of the plates, the passage comprising an inner width that conforms to an outer width of the container; and
   a motion unit that moves the container through the passage along the cooling axis, wherein the sample is cooled by conduction from direct contact between the container and the inner surfaces of the plates,
   wherein the cooling plates maintain direct and tight sliding contact with the flexible container as the flexible container passes through the passage.

2. The apparatus according to claim 1, wherein the plates are oriented vertically.

3. The apparatus according to claim 1, wherein the plates are oriented horizontally.

4. The apparatus according to claim 1, wherein the inner surfaces of the plates are parallel to side walls of the container.

5. The apparatus according to claim 1, further comprising a retention device adapted to hold the container.

6. The apparatus according to claim 1, further comprising two or more sets of cooling plates arranged along the cooling axis adjacent to each other, wherein at least two adjacent sets are separated by a gap.

7. The apparatus according to claim 1, wherein the cooling plates comprise at least one channel adapted for flow of a cryogenic fluid therethough.

8. The apparatus according to claim 7, wherein the cryogenic fluid comprises liquid nitrogen.

9. The apparatus according to claim 1, a feedback control system adapted to control at least one freezing parameter.

10. The apparatus according to claim 9, further comprising a heating arrangement associated with the cooling plates.

11. The apparatus according to claim 10, wherein the heating arrangement comprises at least one electric resistance heater.

12. The apparatus according to claim 9, wherein the feedback control system comprises temperature sensors.

13. The apparatus according to claim 9, wherein the feedback control system comprises a processor.

14. The apparatus according to claim 13, wherein the processor is capable of controlling at least one of flow of cryogenic fluid, pressure of the cryogenic fluid, heating arrangement, and the motion unit.

15. The apparatus according to claim 1, further comprising a monitoring means.

16. The apparatus according to claim 15, wherein the monitoring means comprises a video camera.

17. The apparatus according to claim 15, wherein the monitoring means comprises a device capable of taking a temperature measurement of the biological sample during freezing.

18. The apparatus according to claim 17, wherein the device is an infrared thermograph.

19. The apparatus according to claim 1, further comprising a first chamber adapted to receive the container, a second chamber adapted to perform the freezing, and a third chamber adapted for removal of the container after freezing, the chambers constituting at least a portion of the passage.

20. The apparatus according to claim 19, adapted to initiate freezing within the first chamber.

21. The apparatus according to claim 1, adapted to initiate freezing external to the passage.

22. The apparatus according to claim 21, further adapted to initiate freezing in an area of the container and to introduce the container into the passage after initiation, wherein during the initiation the container is disposed such that the area is near the top thereof, and during introduction into the passage the area is near the front thereof in the direction of the movement.

23. The apparatus according to claim 19, wherein the third chamber is adapted to cool the container to a temperature which is below that achieved as a result of freezing.

24. The apparatus according to claim 1, wherein the cooling axis is disposed vertically.

25. The apparatus according to claim 24, further adapted to initiate freezing internal to the passage, and adapted for movement of the container from a lower portion of the passage to a higher portion of the passage.

26. A method of cooling a biological sample, the method comprising:
 (a) providing the apparatus according to claim 1;
 (b) inserting the container containing a biological sample into the apparatus;
 (c) providing a predetermined temperature gradient along the cooling axis; and
 (d) moving the container through the passage along the cooling axis.

27. The apparatus according to claim 1, wherein when the container is in the apparatus, the biological sample is disposed in the container such that the biological sample remains below the height of the passage.

28. The apparatus according to claim 1, wherein the biological sample comprises red blood cells.

29. The apparatus according to claim 1, wherein the container is a blood bag.

30. The apparatus according to claim 1, wherein the container has a length twenty times larger than the width of the container.

31. The apparatus according to claim 1, wherein the passage has a constant cross section throughout the length of the passage.

32. The apparatus according to claim 1, wherein the width of the passage is adjustable.

33. The apparatus according to claim 1, wherein the cooling plates are configured to adjust to a varying width of the flexible container and maintain direct contact.

34. The apparatus according to claim 33, wherein the cooling plates are configured to automatically adjust to a varying width of the flexible container and maintain direct contact.

35. The apparatus according to claim 1, wherein at least one cooling plate is biased towards a direction of the passage.

36. The apparatus according to claim 1, wherein the inner surfaces of the cooling plates are smooth inner surfaces.

37. The apparatus according to claim 1, wherein the inner surfaces of the cooling plates are parallel to side walls of the flexible container.

38. The apparatus according to claim 1, including the flexible container, the inners surfaces and flexible container configured to provide and maintain direct and tight sliding contact therebetween along a length of the passage.

39. The apparatus according to claim 38, wherein the flexible container is configured to allow an even distribution of the sample against both inner surfaces of the cooling plates.

40. The apparatus according to claim 38, wherein the flexible container and inner surfaces of the cooling plates are smooth further allowing tight contact between the inner surfaces of the cooling plates and the flexible container when the container passes through the passage.

* * * * *